(12) United States Patent
Li

(10) Patent No.: US 11,946,944 B2
(45) Date of Patent: Apr. 2, 2024

(54) ANALYSIS DEVICE FOR DETECTION CHIP, METHOD FOR OPERATING ANALYSIS DEVICE, AND ANALYSIS SYSTEM

(71) Applicants: BEIJING BOE HEALTH TECHNOLOGY CO., LTD., Beijing (CN); BOE TECHNOLOGY GROUP CO., LTD., Beijing (CN)

(72) Inventor: Hongquan Li, Beijing (CN)

(73) Assignees: BEIJING BOE HEALTH TECHNOLOGY CO., LTD., Beijing (CN); BOE TECHNOLOGY GROUP CO., LTD., Beijing (CN)

(*) Notice: Subject to any disclaimer, the term of this patent is extended or adjusted under 35 U.S.C. 154(b) by 690 days.

(21) Appl. No.: 17/255,025

(22) PCT Filed: Jun. 5, 2020

(86) PCT No.: PCT/CN2020/094622
§ 371 (c)(1),
(2) Date: Dec. 22, 2020

(87) PCT Pub. No.: WO2020/259253
PCT Pub. Date: Dec. 30, 2020

(65) Prior Publication Data
US 2021/0263056 A1  Aug. 26, 2021

(30) Foreign Application Priority Data
Jun. 26, 2019  (CN) .......................... 201920971704.1

(51) Int. Cl.
*G01N 35/00*  (2006.01)
*G01D 11/30*  (2006.01)

(52) U.S. Cl.
CPC ....... *G01N 35/00623* (2013.01); *G01D 11/30* (2013.01)

(58) Field of Classification Search
CPC .. G01N 33/00; G01N 35/00; G01N 35/00623; G01D 11/30; G01R 1/04;
(Continued)

(56) References Cited

U.S. PATENT DOCUMENTS

| 5,518,688 A | 5/1996 | Gianino |
| 2005/0048669 A1 | 3/2005 | Hobbs et al. |

(Continued)

FOREIGN PATENT DOCUMENTS

| CN | 105548587 A | 5/2016 |
| CN | 108896775 A | 11/2018 |

(Continued)

OTHER PUBLICATIONS

Extended European Search Report from Application No. 20824066.3 dated Sep. 12, 2022.

*Primary Examiner* — Alexander A Mercado
(74) *Attorney, Agent, or Firm* — Michael J. Musella, Esq.; Dilworth & Barrese, LLP.

(57) ABSTRACT

An analysis device for a detection chip, a method for operating an analysis device, and an analysis system are provided. The analysis device includes a base and a control module. The control module includes a positioning sub-module, an operation sub-module, and a detection sub-module. The positioning sub-module includes an accommodating structure, and the accommodating structure is configured to accommodate the detection chip. The operation sub-module includes at least one operation part, and the at least one operation part is configured to perform a contact mechanical operation. The detection sub-module is configured to perform a detection operation.

18 Claims, 9 Drawing Sheets

(58) Field of Classification Search
CPC . G01R 31/28; B01L 9/50; B01L 9/527; B01L 2200/025; B01L 2200/143; B01L 2300/0663
See application file for complete search history.

(56) References Cited

U.S. PATENT DOCUMENTS

| | | |
|---|---|---|
| 2007/0031283 A1 | 2/2007 | Davis et al. |
| 2011/0048952 A1 | 3/2011 | Van Pelt et al. |
| 2011/0201099 A1 | 8/2011 | Anderson et al. |

FOREIGN PATENT DOCUMENTS

| | | |
|---|---|---|
| CN | 109022274 A | 12/2018 |
| CN | 109470879 A | 3/2019 |
| CN | 210128989 U | 3/2020 |

ANALYSIS DEVICE FOR DETECTION CHIP, METHOD FOR OPERATING ANALYSIS DEVICE, AND ANALYSIS SYSTEM

This application claims the priority of Chinese Patent Application No. 201920971704.1, filed on Jun. 26, 2019, the entire disclosure of which is incorporated herein by reference as part of the disclosure of this application.

TECHNICAL FIELD

Embodiments of the present disclosure relate to an analysis device for a detection chip, a method for operating an analysis device, and an analysis system.

BACKGROUND

At present, equipments with small size in emergency centers or local hospitals develop in a direction of fast, simple, and portable. These equipments with small size are usually named as point-of-care testing (POTC) equipments. Because the POCT equipments have simple operation processes and integrated detection devices, the POCT equipments can be used in emergency department and intensive care unit, which is of great significance to improve the detection process of local hospitals and to realize graded diagnosis and treatment. An analysis device for a detection chip such as a microfluidic chip is a kind of POCT equipment. However, the existing analysis device for the detection chip cannot meet market requirements in terms of portability and detection simplicity.

SUMMARY

At least one embodiment of the present disclosure provides an analysis device for a detection chip, and the analysis device comprises a base and a control module. The control module is provided on the base and comprises a positioning sub-module, an operation sub-module, and a detection sub-module. The positioning sub-module comprises an accommodating structure, and the accommodating structure is configured to accommodate the detection chip. The operation sub-module comprises at least one operation part, and the at least one operation part is configured to be driven to perform a contact mechanical operation on the detection chip. The detection sub-module is configured to perform a detection operation on a sample in the detection chip.

For example, in the analysis device provided by at least one embodiment of the present disclosure, the at least one operation part of the operation sub-module comprises a first operation part, the first operation part comprises a first movable rod, and the first movable rod comprises a first operation end portion and is configured to be driven to a release operation position, so that the first operation end portion performs a release operation on the detection chip.

For example, in the analysis device provided by at least one embodiment of the present disclosure, the first operation part further comprises: a first motor; and a first transmission unit, connected with the first motor and the first movable rod and configured to transmit a motion provided by the first motor to the first movable rod so as to drive the first movable rod.

For example, in the analysis device provided by at least one embodiment of the present disclosure, the first transmission unit comprises: a first lead screw, a first lead screw supporting seat, a first nut, and a first guide rail. The first lead screw is connected with the first motor and configured to rotate under drive of the first motor. The first lead screw is connected between the first lead screw supporting seat and the first motor. The first nut is threadedly engaged with the first lead screw and fixedly connected with the first movable rod, and the first nut is configured, in the case where the first lead screw rotates, to move on the first lead screw. The first movable rod is capable of moving along the first guide rail.

For example, in the analysis device provided by at least one embodiment of the present disclosure, the first operation part further comprises a first position sensor, and the first position sensor is configured, in the case where the first movable rode is in a first position, to generate a first position signal for the first motor.

For example, in the analysis device provided by at least one embodiment of the present disclosure, the at least one operation part of the operation sub-module comprises a second operation part, the second operation part comprises a second movable rod, and the second movable rode comprises a second operation end portion and is configured to be driven to a pressing operation position so as to perform a press operation on the detection chip through the second operation end portion.

For example, in the analysis device provided by at least one embodiment of the present disclosure, the second operation part further comprises: a second motor, configured to drive the second movable rod to move back and forth; and a second transmission unit, connected with the second motor and the second movable rod and configured to transmit a motion provided by the second motor to the second movable rod so as to drive the second movable rod.

For example, in the analysis device provided by at least one embodiment of the present disclosure, the second transmission unit comprises: a second lead screw, a second lead screw supporting seat, a second nut, and a second guide rail. The second lead screw is connected with the second motor and is configured to rotate under drive of the second motor. The second lead screw is connected between the second lead screw supporting seat and the second motor. The second nut is threadedly engaged with the second lead screw and fixedly connected with the second movable rod, and the second nut is configured, in the case where the second lead screw rotates, to move on the second lead screw. The second movable rod is capable of moving along the second guide rail.

For example, in the analysis device provided by at least one embodiment of the present disclosure, the second operation part further comprises a second position sensor, and the second position sensor is configured, in the case where the second movable rod is in a second position, to generate a second position signal for the second motor.

For example, in the analysis device provided by at least one embodiment of the present disclosure, the detection sub-module comprises a movable detection component, and the movable detection component is provided with a U-shaped structure, and is configured to accommodate the detection chip in an opening of the U-shaped structure, move relative to the detection chip, and perform the detection operation.

For example, in the analysis device provided by at least one embodiment of the present disclosure, the detection sub-module further comprises: a third motor, configured to drive the movable detection component to move; and a third transmission unit, connected with the third motor and the movable detection component and configured to transmit a motion provided by the third motor to the movable detection component so as to drive the movable detection component.

For example, in the analysis device provided by at least one embodiment of the present disclosure, the third transmission unit comprises: a third lead screw, a third nut, and a third guide rail. The third lead screw is connected with the third motor and configured to rotate under drive of the third motor. The third nut is threadedly engaged with the third lead screw and fixedly connected with the movable detection component. The third nut is configured, in the case where the third lead screw rotates, to move on the third lead screw. The movable detection component is capable of moving along the third guide rail.

For example, in the analysis device provided by at least one embodiment of the present disclosure, the detection sub-module further comprises a third position sensor, and the third position sensor is configured, in the case where the movable detection component is in a third position, to generate a third position signal for the third motor.

For example, in the analysis device provided by at least one embodiment of the present disclosure, the accommodating structure comprises a accommodating seat, and the positioning sub-module further comprises: a fourth motor, configured to drive the accommodating seat to move; and a fourth position sensor, provided at a moving path of the accommodating seat driven by the fourth motor and configured, in the case where the accommodating seat is in a fourth position, to generate a fourth position signal for the fourth motor.

For example, in the analysis device provided by at least one embodiment of the present disclosure, the accommodating seat is configured to move between the fourth position and a fifth position under drive of the fourth motor; at the fourth position, the accommodating seat is spaced apart from a fixing plate that is matched with the accommodating seat so as to accommodate the detection chip; and at the fifth position, the detection chip is capable of abutting against the fixing plate.

For example, in the analysis device provided by at least one embodiment of the present disclosure, the accommodating structure further comprises a positioning element, and the positioning element is connected with the accommodating seat and is configured, in the case where the detection chip is on the accommodating seat, to position the detection chip in a releasable way.

For example, in the analysis device provided by at least one embodiment of the present disclosure, the positioning element comprises a ball plunger.

For example, in the analysis device provided by at least one embodiment of the present disclosure, the positioning sub-module, the operation sub-module, and the detection sub-module are fixed on a same fixing frame on the base.

For example, in the analysis device provided by at least one embodiment of the present disclosure, the operation sub-module comprises two operation parts, and the two operation parts are respectively located at two opposite sides of the accommodating structure of the positioning sub-module.

For example, the analysis device provided by at least one embodiment of the present disclosure further comprises: a processing module, in signal connection with the control module and configured to provide a control instruction to the control module so as to control operations of the control module; a power supply module, configured to provide electric power to the control module and the processing module; and an interface module, in signal connection with the processing module. The processing module communicates with an external equipment through the interface module. The processing module, the power supply module, and the interface module are all on the base.

At least one embodiment of the present disclosure provides an analysis system, which comprises: a detection chip; and the analysis device described above.

At least one embodiment of the present disclosure provides a method for operating the analysis device described above. The method comprises: performing the contact mechanical operation on the detection chip accommodated in the accommodating structure through the operation sub-module; and performing the detection operation on the detection chip through the detection sub-module.

BRIEF DESCRIPTION OF THE DRAWINGS

Hereinafter, the drawings accompanying embodiments of the present disclosure are simply introduced in order to more clearly explain technical solution(s) of the embodiments of the present disclosure. Obviously, the described drawings below are merely related to some of the embodiments of the present disclosure without constituting any limitation thereto.

DETAILED DESCRIPTION

Figure 1:
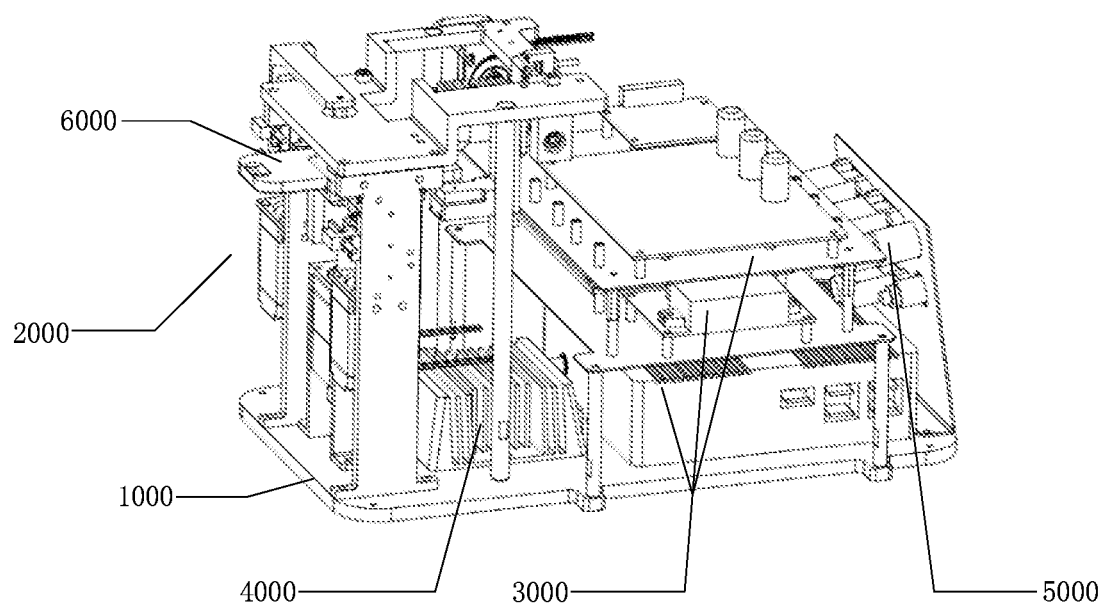
FIG. 1 is a structural schematic diagram of an analysis device for a detection chip according to at least one embodiment of the present disclosure.

In order to make objectives, technical details and advantages of the embodiments of the present disclosure apparent, the technical solutions of the embodiments will be described in a clearly and fully understandable way in connection with the drawings related to the embodiments of the present disclosure. Apparently, the described embodiments are just a portion but not all of the embodiments of the present disclosure. Based on the described embodiments herein, those skilled in the art can obtain other embodiment(s), without any inventive work, which should be within the scope of the present disclosure.

Unless otherwise defined, all the technical and scientific terms used herein have the same meanings as commonly understood by one of ordinary skill in the art to which the present disclosure belongs. The terms "first," "second," etc., which are used in the present disclosure, are not intended to indicate any sequence, amount or importance, but distinguish various components. Similarly, the terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "on," "under," "left," "right" and the like are only used to indicate relative position relationship, and when the position of the described object is changed, the relative position relationship may be changed accordingly.

In order to keep the following descriptions of embodiments of the present disclosure clear and concise, detailed descriptions of known functions and known components are omitted in the present disclosure.

Microfluidic chip technology integrates basic operation units such as sample preparation, reaction, separation, and detection involved in fields such as biology, chemistry, and medicine into a chip with micro-channels to automatically complete the whole process of reaction and analysis. The chip used in this process is called as a microfluidic chip, and the microfluidic chip can also be called as Lab-on-a-chip. Because the microfluidic chip technology has the advantages of less sample consumption, fast analysis speed, easy to be made into portable instruments, and suitable for instant and on-site analysis, etc., the microfluidic chip technology has been widely used in many fields such as biology, chemistry, and medicine. The microfluidic chip can be implemented in various types, and the embodiments of the present disclosure do not limit the specific structure of the microfluidic chip.

As mentioned above, the existing analysis device for a detection chip such as the microfluidic chip is difficult to meet the market requirements in terms of portability and detection simplicity.

At least one embodiment of the present disclosure provides an analysis device for a detection chip, and the analysis device can realize portability of instruments and simplicity of detection.

FIG. 1 is a structural schematic diagram of an analysis device for a detection chip according to at least one embodiment of the present disclosure. As illustrated in FIG. 1, an analysis device for a detection chip according to at least one embodiment of the present disclosure includes a base 1000 and a control module 2000. The base 1000 is configured to support and fix the control module 2000. For example, the base 1000 can be manufactured by rigid materials such as metal, glass, etc. Hereinafter, the embodiments of the present disclosure will be described by taking the case where the detection chip is a microfluidic chip as an example. However, it should be understood that the embodiments of the present disclosure are not limited thereto.

Figure 2:
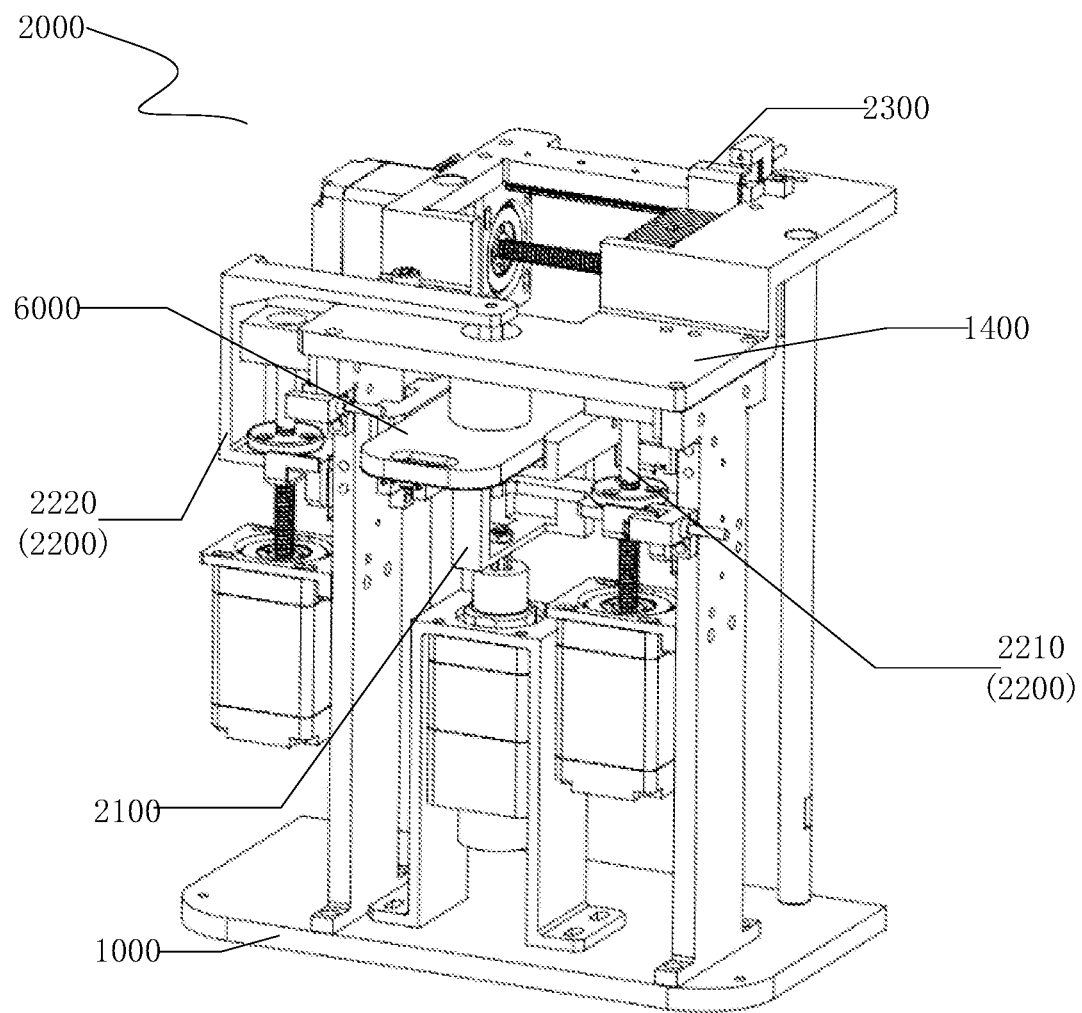
FIG. 2 is a structural schematic diagram of the control module in FIG. 1.

FIG. 2 is a structural schematic diagram of the control module in FIG. 1. As illustrated in FIG. 2, the control module 2000 includes a positioning sub-module 2100, an operation sub-module 2200, and a detection sub-module 2300. In some drawings of the present disclosure (for example, the above-mentioned FIG. 1 and FIG. 2, and FIG. 9-FIG. 12 which will be described later), for the convenience of description, a microfluidic chip 6000, which is provided in the analysis device in actual operation, is also illustrated in the figures. However, it should be understood that the microfluidic chip 6000 is not included as an integral part of the analysis device according to the embodiments of the present disclosure, but the microfluidic chip 6000 is installed in or is removed from the analysis device as required. According to at least one embodiment of the present disclosure, the positioning sub-module 2100, the operation sub-module 2200, and the detection sub-module 2300 of the control module 2000 are in the same analysis device, so that the realization of portable analysis device can be facilitated. For example, the portable and automatic analysis device can be further realized.

As illustrated in FIG. 2, the analysis device for the detection chip according to at least one embodiment of the present disclosure may further include a fourth fixing plate 1400, and the fourth fixing plate 1400 cooperates with the positioning sub-module 2100 so as to sandwich the microfluidic chip 6000 therebetween, thereby fixing the microfluidic chip 6000.

The operation sub-module includes at least one operation part, and the at least one operation part is configured to be driven to perform a contact mechanical operation on the microfluidic chip. In different embodiments, the contact mechanical operation is of many types, such as a releasing operation, a pressing operation, etc. For example, a puncturing operation can also be performed in order to realize the releasing operation.

Figure 3:
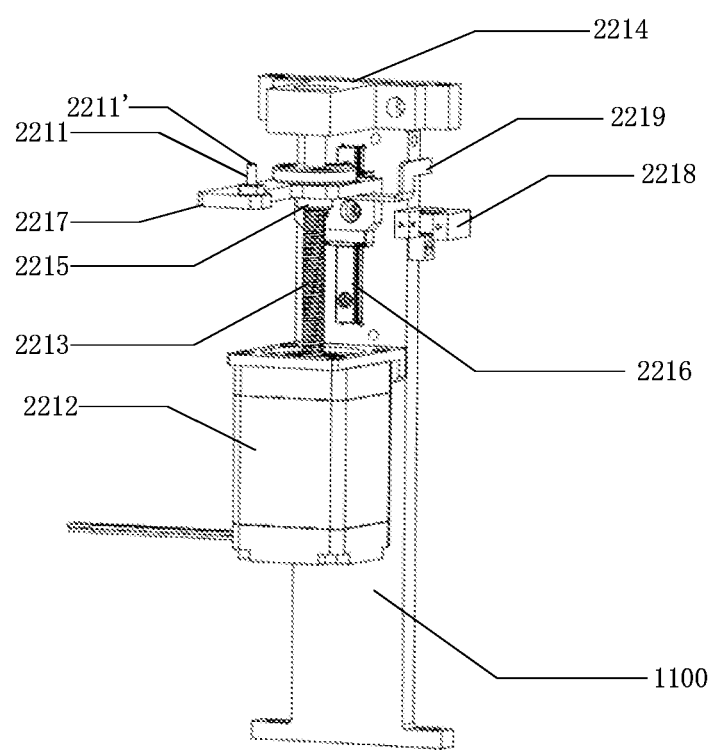
FIG. 3 is a structural schematic diagram of a first operation part according to at least one embodiment of the present disclosure.

In some embodiments, the at least one operation part of the operation sub-module 2200 may include a first operation part 2210, and the first operation part 2210 is configured to allow a sample sealed inside the microfluidic chip in advance to enter a flow channel of the microfluidic chip. FIG. 3 is a structural schematic diagram of a first operation part according to at least one embodiment of the present disclosure. As illustrated in FIG. 3, the first operation part 2210 includes a first movable rod 2211. The first movable rod 2211 includes a first operation end portion 2211', and the first movable rod 2211 is configured to be driven to a release operation position, so that the first operation end portion 2211' performs a release operation on the microfluidic chip. In some embodiments, the release operation may include breaking a membrane defining (for example, sealing) the sample (or reagent) in the microfluidic chip, thereby forming a flow path for detecting the sample. The flow path allows the sample to be released into the flow channel of the microfluidic chip through the broken membrane. For example, in some embodiments, the first operation end portion 2211' may be in a cylindrical shape, a tapered shape, or in any suitable shapes, so that the first operation end portion 2211' is capable of breaking the membrane defining the sample in the microfluidic chip in the case where the first operation end portion 2211' is driven to the release operation position, thereby forming the flow path for the sample. In some embodiments, the first operation end portion 2211' may be positioned to be in contact with the microfluidic chip during the release operation. In an exemplary embodiment, the first movable rod 2211 may be in a tapered shape, and the first operation end portion 2211' may be in a dome shape, so that a protective film in the microfluidic chip is prevented from being pierced in the case where the first operation end portion 2211' is capable of breaking the membrane defining the sample in the microfluidic chip.

In some embodiments, the first operation part 2210 further includes a first motor 2212 and a first transmission unit. The first transmission unit is connected with the first motor 2212 and the first movable rod 2211, and is configured to transmit the motion provided by the first motor 2212 to the first movable rod 2211 so as to drive the first movable rod 2211. It should be understood that although FIG. 3 shows that the first movable rod 2211 is driven by the first motor 2212, in some other embodiments, the first movable rod 2211 may be manually operated, which is not limited in the embodiments of the present disclosure.

The first operation part 2210 will be described below by taking the case where the first motor 2212 and the first transmission unit adopt the combination of a rotary motor and a lead screw as an example. However, it should be understood that the present disclosure is not limited to this. For example, in some other embodiments, the first motor 2212 may also be a linear motor, and the first transmission unit is a connection component between the first motor 2212 and the first movable rod 2211.

As illustrated in FIG. 3, the first transmission unit includes a first lead screw 2213, a first lead screw supporting seat 2214, a first nut 2215, and a first guide rail 2216. The first lead screw 2213 is connected with the first motor 2212 and is configured to rotate under the drive of the first motor 2212. The first lead screw 2213 is connected between the first lead screw supporting seat 2214 and the first motor 2212, and the first lead screw supporting seat 2214 is fixed relative to the first lead screw 2213 and the first motor 2212. For example, the first lead screw supporting seat 2214 may be a ball lead screw support seat, but the embodiments of the present disclosure are not limited thereto. Unfavorable torque can be avoided by arrangement of the first lead screw supporting seat 2214.

The first nut 2215 is threadedly engaged with the first lead screw 2213 and is fixedly connected with the first movable rod 2211. The first nut 2215 is configured, in the case where the first lead screw 2213 rotates, to move on the first lead screw 2213. The first nut 2215 is slidably connected with the first guide rail 2216, and the first guide rail 2216 acts to restrain the first nut 2215, so that the first movable rod 2211 connected with the first nut can move along the first guide rail 2216. The first nut 2215 may be directly connected with the first guide rail 2216, or the first nut 2215 may be connected with the first guide rail 2216 through other elements (for example, a first supporting plate 2217), which is not limited in the embodiments of the present disclosure.

In some embodiments, the first movable rod 2211 may be fixedly connected with the first nut 2215 through the first supporting plate 2217. However, in some other embodiments, the first movable rod 2211 may also be directly connected with the first nut 2215, or the first movable rod 2211 may be integrally formed with the first nut 2215, which is not limited in the embodiments of the present disclosure.

In some embodiments, the first operation part 2210 may further include a first position sensor 2218, and the first position sensor 2218 is configured, in the case where the first movable rod 2211 is in a first position, to generate a first position signal for the first motor 2212. For example, the first position corresponds to an origin position of the first motor 2212, the first position signal is used to reset the first motor 2212, and the first position sensor 2218 can send the first position signal generated in the case where the first movable rod 2211 is in the first position to the control module that controls the first motor 2212, so that the first motor 2212 is reset under the control of the control module. By arrangement of the first position sensor 2218, the origin position of the first motor 2212 can be reset, so that the first movable rod 2211 can be accurately positioned.

In some embodiments, the first operation part may further include a first fixing plate 1100. The first lead screw supporting seat 2214 can be fixedly connected to the base 1000 through the first fixing plate 1100. The first motor 2212, the first guide rail 2216, and the first position sensor 2218 can be fixed on the first fixing plate 1100, but the embodiments of the present disclosure are not limited to this case. In some other embodiments, the first motor 2212, the first guide rail 2216, and the first position sensor 2218 can be fixed on two or more fixing plates and can be fixedly connected with the base 1000 through these fixing plates. In addition, in some embodiments, the first lead screw supporting base 2214 can also be integrally formed with the first fixing plate 1100, which is not limited in the embodiments of the present disclosure.

In some embodiments, the first position sensor 2218 may include a signal emitting part configured to emit a detection signal and a signal receiving part configured to receive the detection signal emitted by the signal emitting part, and the first position sensor 2218 may generate an indication signal in the case where the signal receiving part does not receive the detection signal emitted by the signal emitting part. In this case, the first operation part may further include a first stopper piece 2219, the first stopper piece 2219 can be fixedly connected with the first supporting plate 2217 so as to move synchronously with the first movable rod 2211, and the first stopper piece 2219 is arranged between the signal emitting part and the signal receiving part of the first position sensor 2218 in the case where the first movable rod 2211 is in the first position, so that the signal receiving part cannot receive the detection signal emitted by the signal emitting part, thus enabling the first position sensor 2218 to generate the first position signal. However, it should be understood that the first stopper piece 2219 can also be fixedly connected with at least one selected from the group consisting of the first supporting plate 2217, the first nut 2215, and the first movable rod 2211, which is not limited in the embodiments of the present disclosure.

For example, the first position sensor 2218 may include a groove-type photoelectric switch, and the first stopper piece 2219 may be configured to be accommodated in the groove of the groove-type photoelectric switch and to prevent the signal emitted by a signal emitting end of the groove-type photoelectric switch from reaching a signal receiving end of the groove-type photoelectric switch. The first stopper piece 2219 can be manufactured by any suitable materials such as metal, wood, plastic, etc., as long as the first stopper piece 2219 can prevent the signal emitted by the signal emitting end of the groove-type photoelectric switch from reaching the signal receiving end of the groove-type photoelectric switch. However, it should be understood that embodiments of the present disclosure are not limited thereto. For example, in some other embodiments, the first position sensor 2218 may also be a proximity sensor arranged at the first position, and in the case where the first position sensor 2218 detects that a distance from the first position sensor 2218 to the first movable rod 2211 is less than a preset value, it can be determined that the first movable rod 2211 is at the first position.

Figure 4:
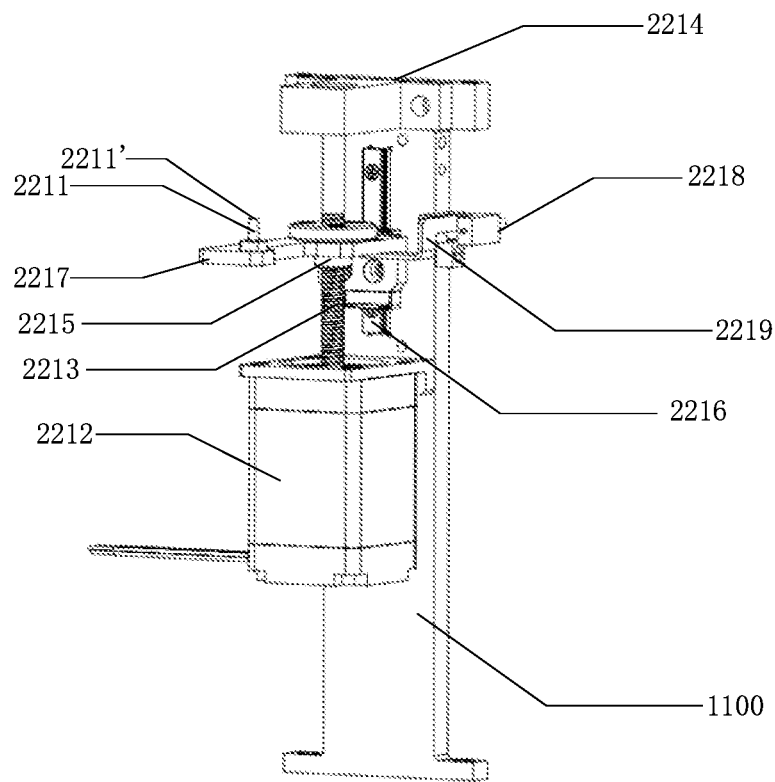
FIG. 4 is a schematic diagram of a first movable rod in a first position according to at least one embodiment of the present disclosure.
Figure 5:
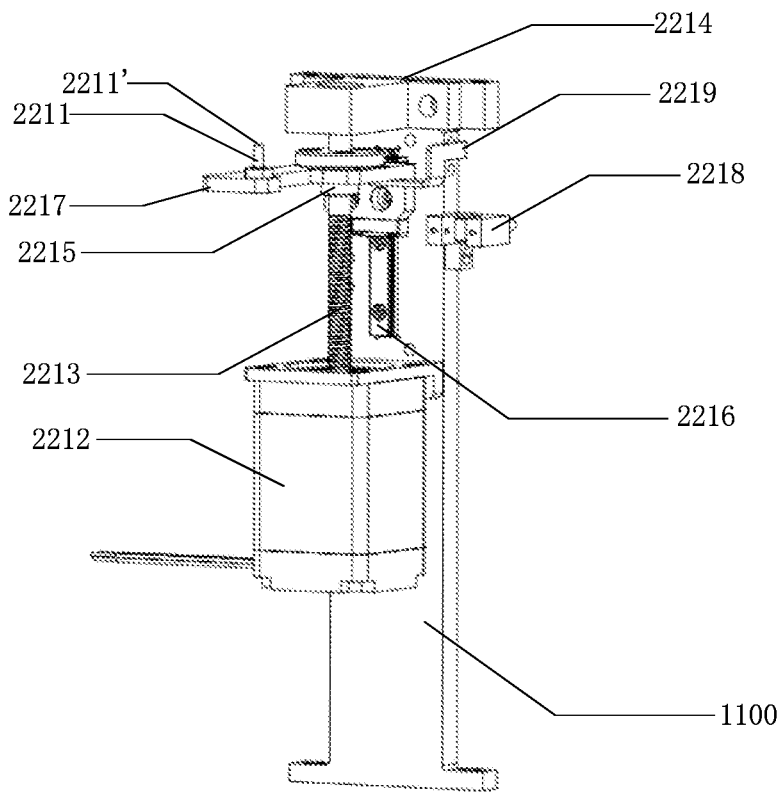
FIG. 5 is a schematic diagram of a first movable rod in a release operation position according to at least one embodiment of the present disclosure.

In the embodiments of the present disclosure, the first movable rod 2211 is capable of moving between the first position and the release operation position under the drive of the first motor 2212. FIG. 4 is a schematic diagram of the first movable rod 2211 in the first position according to at least one embodiment of the present disclosure, and FIG. 5 is a schematic diagram of the first movable rod 2211 in the release operation position according to at least one embodiment of the present disclosure. In the case where the first movable rod 2211 is at the release operation position, the first operation end portion 2211' of the first movable rod 2211 contacts the microfluidic chip placed in the analysis device and can perform the release operation on the microfluidic chip. For example, in some embodiments, in the case where the first movable rod 2211 is in the release operation position, the first nut 2215 may be located at the farthest end of the first lead screw 2213 away from the first motor 2212. It should be understood that the distance between the first position and the release operation position can be set according to actual requirements.

Figure 6:
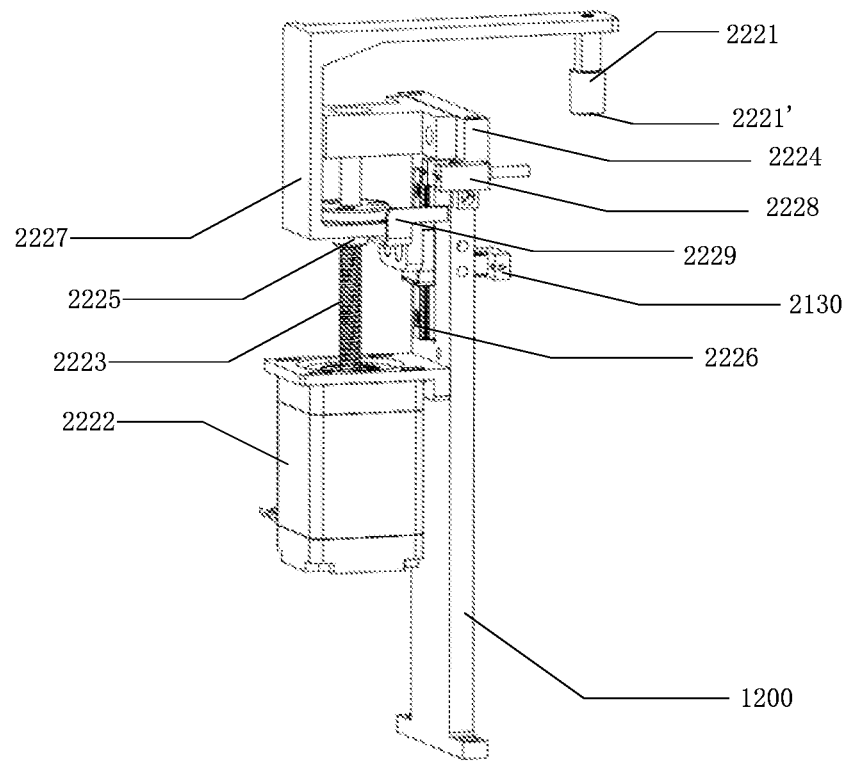
FIG. 6 is a structural schematic diagram of a second operation part according to at least one embodiment of the present disclosure.

In some embodiments, the at least one operation part of the operation sub-module 2200 may further include a second operation part 2220. FIG. 6 is a structural schematic diagram of a second operation part according to at least one embodiment of the present disclosure. As illustrated in FIG. 6, the second operation part 2220 includes a second movable rod 2221. The second movable rod 2221 includes a second operation end portion 2221', and the second movable rod 2221 is configured to be driven to a pressing operation position, so that the second operation end portion 2221' performs a pressing operation on the microfluidic chip. In some embodiments, the pressing operation may include pressing an elastic compressible driver in the microfluidic chip for driving the sample flow, such as a membrane pump configured to drive the sample flow. For example, the second movable rod 2221 may be configured to move back and forth relative to the microfluidic chip, so that the second operation end portion 2221' is in contact with the microfluidic chip and presses or leaves the elastic compressible driver which is configured to drive the sample flow in the microfluidic chip. By alternately pressing and leaving the elastic compressible driver through the second movable rod 2221, the sample can leave or return to the elastic compressible driver or a storage chamber connected with the elastic compressible driver, so that preset operations, such as a dilution operation, a liquid feeding operation, a mixing operation, a cleaning operation, etc., can be performed on the sample. In some embodiments, the second movable rod 2221 may be positioned in contact with the microfluidic chip during the pressing operation. In addition, in some embodiments, the second operation end portion 2221' may be in a column shape, a rectangular parallelepiped shape, or in any suitable shapes, so that, in the case where the second movable rod 2221 is driven to the pressing operation position, the second operation end portion 2221' is capable of applying a force to the elastic compressible driver which is configured to drive the sample flow in the microfluidic chip without damaging the microfluidic chip.

Referring to FIG. 2, in some embodiments, the fourth fixing plate 1400 may further have a hole through which the second movable rod 2221 of the second operation part 2220 passes to perform the pressing operation on the microfluidic chip 6000.

In some embodiments, the second operation part 2220 further includes a second motor 2222 and a second transmission unit. The second motor 2222 is configured to drive the second movable rod 2221 to move back and forth. The second transmission unit is connected with the second motor 2222 and the second movable rod 2221, and is configured to transmit the motion provided by the second motor 2222 to the second movable rod 2221 so as to drive the second movable rod 2221. It should be understood that although FIG. 6 shows that the second movable rod 2221 is driven by the second motor 2222, in some other embodiments, the second movable rod 2221 may be manually operated, which is not limited in the embodiments of the present disclosure.

Next, the second operation part 2220 will be described by taking the case where the second motor 2222 and the second transmission unit adopt the combination of a rotary motor and a lead screw as an example. However, it should be understood that the present disclosure is not limited to this. For example, in some other embodiments, the second motor 2222 may also be a linear motor, and the second transmission unit is a connection component between the second motor 2222 and the second movable rod 2221.

As illustrated in FIG. 6, the second transmission unit includes a second lead screw 2223, a second lead screw supporting seat 2224, a second nut 2225, and a second guide rail 2226. The second lead screw 2223 is connected with the second motor 2222, and is configured to rotate under the drive of the second motor 2222. The second lead screw 2223 is connected between the second lead screw supporting seat 2224 and the second motor 2222, and the second lead screw supporting seat 2224 is fixed relative to the second motor 2222 and the second lead screw 2223. For example, the second screw supporting seat 2224 may be a ball lead screw supporting seat, but the embodiments of the present disclosure are not limited thereto. Unfavorable torque can be avoided by arrangement of the second lead screw supporting seat 2224.

The second nut 2225 is threadedly engaged with the second lead screw 2223 and is fixedly connected with the second movable rod 2221. The second nut 2225 is configured, in the case where the second lead screw 2223 rotates, to move on the second lead screw 2223. The second nut 2225 is slidably connected with the second guide rail 2226, and the second guide rail 2226 acts to restrain the second nut 2225, so that the second movable rod 2221 connected with the second nut 2225 can move along the second guide rail 2226. The second nut 2225 may be directly connected with the second guide rail 2226, or the second nut 2225 may be connected with the second guide rail 2226 through other elements (for example, a second supporting plate 2227), which is not limited in the embodiments of the present disclosure.

In some embodiments, the second movable rod 2221 may be fixedly connected with the second nut 2225 through the second supporting plate 2227. However, in some other embodiments, the second movable rod 2221 may also be directly connected with the second nut 2225, or the second movable rod 2221 may be integrally formed with the second nut 2225, which is not limited in the embodiments of the present disclosure.

In some embodiments, the second operation part 2220 further includes a second position sensor 2228, and the second position sensor 2228 is configured, in the case where the second movable rod 2221 is in a second position, to generate a second position signal for the second motor 2222. For example, the second position corresponds to an origin position of the second motor 2222, the second position signal is used to reset the second motor 2222, and the second position sensor 2228 can send the second position signal generated in the case where the second movable rod 2221 is in the second position to the control module that controls the second motor 2222, so that the second motor 2222 is reset under the control of the control module. By arrangement of the second position sensor 2228, the origin position of the second motor 2222 can be reset, so that the second movable rod 2221 can be accurately positioned.

In some embodiments, the second operation part 2220 may further include a second fixing plate 1200. The second lead screw supporting seat 2224 can be fixedly connected with the base 1000 through the second fixing plate 1200. The second motor 2222, the second guide rail 2226, and the second position sensor 2228 can be fixed on the second fixing plate 1200, but the embodiments of the present disclosure are not limited to this. In some other embodiments, the second motor 2222, the second guide rail 2226, and the second position sensor 2228 can be fixed on two or more fixing plates and are fixedly connected on the base 1000 through these fixing plates. In addition, in some embodiments, the second fixing plate 1200 can also be integrally formed with the second lead screw supporting seat 2224, which is not limited in the embodiments of the present disclosure.

In some embodiments, the second position sensor 2228 may include a signal emitting part for emitting a detection signal and a signal receiving part for receiving the detection signal emitted by the signal emitting part, and the second position sensor 2228 may generate an indication signal in the case where the signal receiving part does not receive the detection signal emitted by the signal emitting part. In this case, the second operation part may further include a second stopper piece 2229, the second stopper piece 2229 can be fixedly connected with the second supporting plate 2227 so as to move synchronously with the second movable rod 2221, and the second stopper piece 2229 is arranged between the signal emitting part and the signal receiving part of the second position sensor 2228 in the case where the second movable rod 2221 is in the second position, so that the signal receiving part cannot receive the detection signal emitted by the signal emitting part, thus enabling the second position sensor 2228 to generate the second position signal. However, it should be understood that the second stopper piece 2229 can also be fixedly connected with at least one selected from the group consisting of the second supporting plate 2227, the second nut 2225, and the second movable rod 2221, which is not limited in the embodiments of the present disclosure.

For example, the second position sensor 2228 may include a groove-type photoelectric switch, and the second stopper piece 2229 may be configured to be accommodated in the groove of the groove-type photoelectric switch and to prevent the signal emitted by a signal emitting end of the groove-type photoelectric switch from reaching a signal receiving end of the groove-type photoelectric switch. The second stopper piece 2229 can be manufactured by any suitable materials such as metal, wood, plastic, etc., as long as the second stopper piece 2229 can prevent the signal emitted by the signal emitting end of the groove-type photoelectric switch from reaching the signal receiving end of the groove-type photoelectric switch. However, it should be understood that the embodiments of the present disclosure are not limited thereto. For example, in some other embodiments, the second position sensor 2228 may also be a proximity sensor arranged at the second position, and in the case where the second position sensor 2228 detects that a distance between the second position sensor 2228 and the second movable rod 2221 is less than a preset value, it is determined that the second movable rod 2221 is at the second position.

Figure 7:
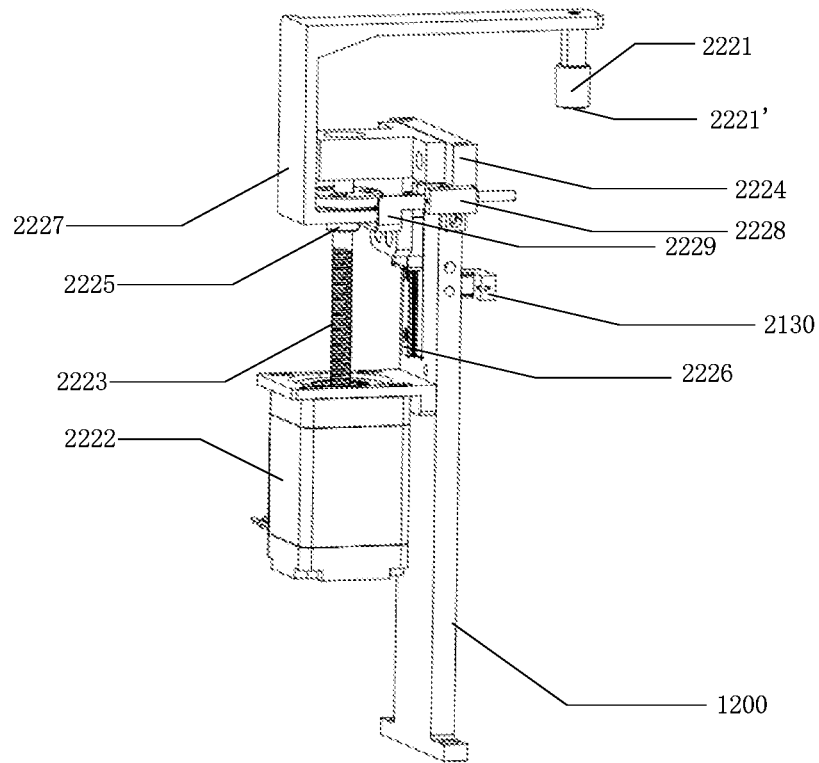
FIG. 7 is a schematic diagram of a second movable rod in a second position according to at least one embodiment of the present disclosure.
Figure 8:
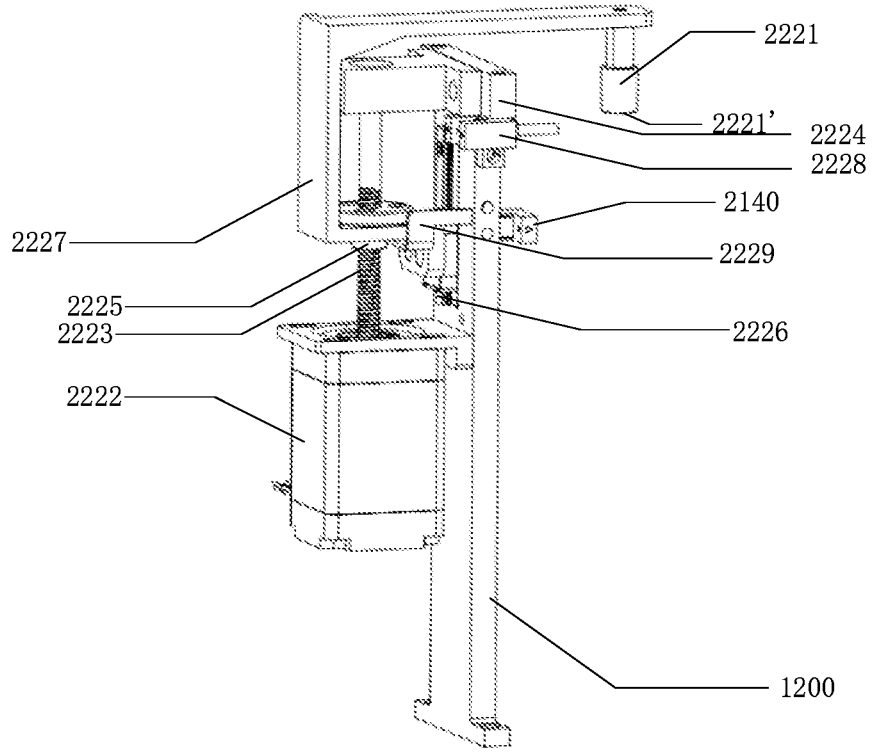
FIG. 8 is a schematic diagram of a second movable rod in a pressing operation position according to at least one embodiment of the present disclosure.

In some embodiments, the second movable rod 2221 is capable of moving between the second position and the pressing operation position under the drive of the second motor 2222. FIG. 7 is a schematic diagram of the second movable rod 2221 in the second position according to at least one embodiment of the present disclosure, and FIG. 8 is a schematic diagram of the second movable rod 2221 in the pressing operation position according to at least one embodiment of the present disclosure. In the case where the second movable rod 2221 is in the pressing operation position, the second operation end portion 2221' of the second movable rod 2221 contacts the microfluidic chip placed in the analysis device and can press or release the elastic compressible driver which is configured to drive the sample flow in the microfluidic chip. For example, in some embodiments, in the case where the second movable rod 2221 is at the pressing operation position, the second nut 2225 may be located at the farthest end of the second lead screw 2223 away from the second motor 2222. It should be understood that the distance between the second position and the pressing operation position can be set according to actual requirements.

In some embodiments, the first operation part 2210 and the second operation part 2220 may be located on two opposite sides of the accommodating structure of the positioning sub-module 2100. For example, the direction in which the first movable rod 2211 moves toward the microfluidic chip may be opposite to the direction in which the second movable rod 2221 moves toward the microfluidic chip, so that the first operation part 2210 and the second operation part 2220 can be arranged more conveniently, which contributes to the miniaturization of the analysis device.

Figure 9:
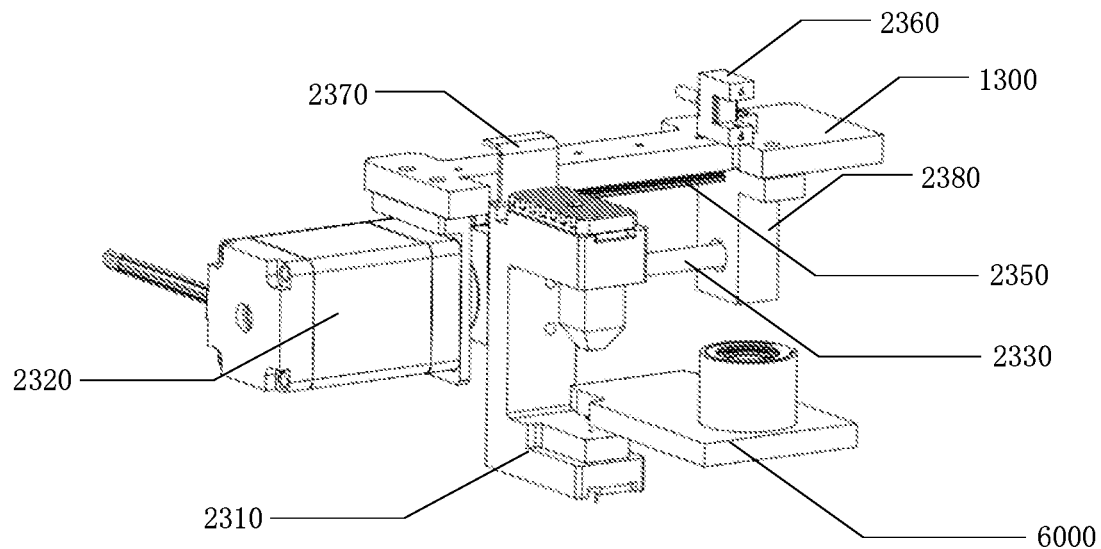
FIG. 9 is a structural schematic diagram of a detection sub-module according to at least one embodiment of the present disclosure.

FIG. 9 is a structural schematic diagram of a detection sub-module according to at least one embodiment of the present disclosure. The detection sub-module according to at least one embodiment of the present disclosure is configured to perform a detection operation on a sample in the microfluidic chip. As illustrated in FIG. 9, the detection sub-module 2300 includes a movable detection component 2310. For example, the movable detection component 2310 may have a U-shaped structure, and the movable detection component 2310 is configured to accommodate the microfluidic chip 6000 in an opening of the U-shaped structure, move relative to the microfluidic chip 6000, and perform the detection operation. However, it should be understood that the movable detection component 2310 can also have other shapes, and the embodiments of the present disclosure are not limited to this.

The movable detection component 2310 is, for example, an optical detection component, and the optical detection component may include a light source, a sensor, etc. for performing a biochemical detection. The light source may include, for example, a point light source, a line light source, a plane light source, etc. The light source can be, for example, a light emitting diode, a cold cathode fluorescent lamp, an electroluminescent light source, a flat fluorescent lamp, a laser light source, etc., and the emitted light by the light source can be visible light, infrared light, etc., which is not limited in the embodiments of the present disclosure. The sensor may include, for example, an optical sensor, a temperature sensor, etc. The optical sensor can be, for example, a photodiode, a phototransistor, etc. For example, the photodiode can be a PIN diode, a PN diode, etc., and may be a silicon-based diode, or a non-silicon-based diode, etc. The embodiments of the present disclosure do not limit the specific type and structure of the movable detection component 2310. According to the parameters to be detected, the movable detection component 2310 can adopt different light sources or sensors. For example, in some embodiments, the movable detection component 2310 may include an optical sensor to detect a luminous intensity or an absorbance of the sample in the microfluidic chip 6000. In some other embodiments, the movable detection component 2310 may include a light source to detect components of the sample in the microfluidic chip 6000. In still some other embodiments, the movable detection component 2310 may include a light source and an optical sensor to detect a fluorescence intensity of the sample in the microfluidic chip 6000.

In some embodiments, the detection sub-module 2300 further includes a third motor 2320 and a third transmission unit. The third motor 2320 is configured to drive the movable detection component 2310 to move. The third transmission unit is connected with the third motor 2320 and the movable detection component 2310, and is configured to transmit the motion provided by the third motor 2320 to the movable detection component 2310 so as to drive the movable detection component 2310. It should be understood that although FIG. 9 shows that the movable detection component 2310 is driven by the third motor 2320, in some other embodiments, the movable detection component 2310 may be manually operated, which is not limited in the embodiments of the present disclosure.

Next, the detection sub-module 2300 will be described by taking the case where the third motor 2320 and the third transmission unit adopt the combination of a rotary motor and a lead screw as an example. However, it should be understood that the present disclosure is not limited to this. For example, in some other embodiments, the third motor 2320 may also be a linear motor, and the third transmission unit is a connection component between the third motor 2320 and the movable detection component 2310.

As illustrated in FIG. 9, the third transmission unit includes a third lead screw 2330, a third nut 2340, and a third guide rail 2350. The third lead screw 2330 is connected with the third motor 2320, and is configured to rotate under the drive of the third motor 2320. The third nut 2340 is threadedly engaged with the third lead screw 2330 and is fixedly connected with the movable detection component 2310. The third nut 2340 is configured, in the case where the third lead screw 2330 rotates, to move on the third lead screw 2330. The third nut 2340 is slidably connected with the third guide rail 2350, and the third guide rail 2350 acts to restrain the third nut 2340, and the movable detection component 2310 can move along the third guide rail 2350. The third nut 2340 may be directly connected with the third guide rail 2350, or the third nut 2340 may be connected with the third guide rail 2350 through other elements (for example, the movable detection component 2310), which is not limited in the embodiments of the present disclosure.

The movable detection component 2310 may be detachably connected with the third nut 2340, or may be fixedly connected with the third nut 2340. The movable detection component 2310 may be directly connected with the third nut 2340, or may be integrally formed with the third nut 2340, or may be fixedly connected with the third nut 2340 through other elements, which is not limited in the embodiments of the present disclosure.

In some embodiments, the detection sub-module 2300 may further include a third position sensor 2360. The third position sensor 2360 is configured, in the case where the movable detection component 2310 is in a third position, to generate a third position signal for the third motor 2320. For example, the third position corresponds to an origin position of the third motor 2320, the third position signal is used to reset the third motor 2320, and the third position sensor 2360 can send the third position signal generated in the case where the movable detection component 2310 is in the third position to the control module that controls the third motor 2320, so that the third motor 2320 is reset under the control of the control module. By arrangement of the third position sensor 2360, the origin position of the third motor 2320 can be reset, so that the movable detection component 2310 can be accurately positioned.

In some embodiments, the detection sub-module 2300 may further include a third lead screw supporting seat 2380. The third lead screw 2330 is connected between the third lead screw supporting seat 2380 and the third motor 2320, and the third lead screw supporting seat 2380 is fixed relative to the third lead screw 2330 and the third motor 2320. For example, the third screw supporting seat 2380 may be a ball lead screw supporting seat, but the embodiments of the present disclosure are not limited thereto. However, in some other embodiments, the detection sub-module 2300 may not include the third lead screw supporting seat 2380, and a limiting member, such as a limiting post, a limiting nut, etc., may be arranged at the end of the third lead screw 2330 away from the third motor 2320, which is not limited in the embodiments of the present disclosure.

In some embodiments, the detection sub-module 2300 may further include a third fixing plate 1300. The third motor 2320, the third guide rail 2350, and the third position sensor 2360 can be fixed on the third fixing plate 1300. However, the embodiments of the present disclosure are not limited thereto. In some other embodiments, the third motor 2320, the third guide rail 2350, and the third position sensor 2360 may be fixed on two or more fixing plates. In addition, in some embodiments, the third fixing plate 1300 can also be integrally formed with the third lead screw supporting seat 2380, which is not limited in the embodiments of the present disclosure.

In some embodiments, the third position sensor 2360 may include a signal emitting part for emitting a detection signal and a signal receiving part for receiving the detection signal emitted by the signal emitting part, and the third position sensor 2360 may generate an indication signal in the case where the signal receiving part does not receive the detection signal emitted by the signal emitting part. In this case, the detection sub-module 2300 may further include a third stopper piece 2370, and the third stopper piece 2370 can be fixedly connected with the movable detection component 2310 so as to move synchronously with the movable detection component 2310, and the third stopper piece 2370 is arranged between the signal emitting part and the signal receiving part of the third position sensor 2360 in the case where the movable detection component 2310 is in the third position, so that the signal receiving part cannot receive the detection signal emitted by the signal emitting part, so that the third position sensor 2360 generates the third position signal. However, it should be understood that the third stopper piece 2370 can also be fixedly connected with at least one selected from the group of the third nut 2340 and the movable detection component 2310, which is not limited in the embodiments of the present disclosure.

For example, the third position sensor 2360 may include a groove-type photoelectric switch, and the third stopper piece 2370 may be configured to be accommodated in the groove of the groove-type photoelectric switch and to prevent the signal emitted by a signal emitting end of the groove-type photoelectric switch from reaching a signal receiving end of the groove-type photoelectric switch. The third stopper piece 2370 can be manufactured by any suitable materials such as metal, wood, plastic, etc., as long as the third stopper piece 2370 can prevent the signal emitted by the signal emitting end of the groove-type photoelectric switch from reaching the signal receiving end of the groove-type photoelectric switch. However, it should be understood that the embodiments of the present disclosure are not limited thereto. For example, in some other embodiments, the third position sensor 2360 may also be a proximity sensor arranged at the third position, and in the case where the third position sensor 2360 detects that a distance between the third position sensor 2360 and the movable detection component 2310 is less than a preset value, it is determined that the movable detection component 2310 is at the third position.

Figure 10:
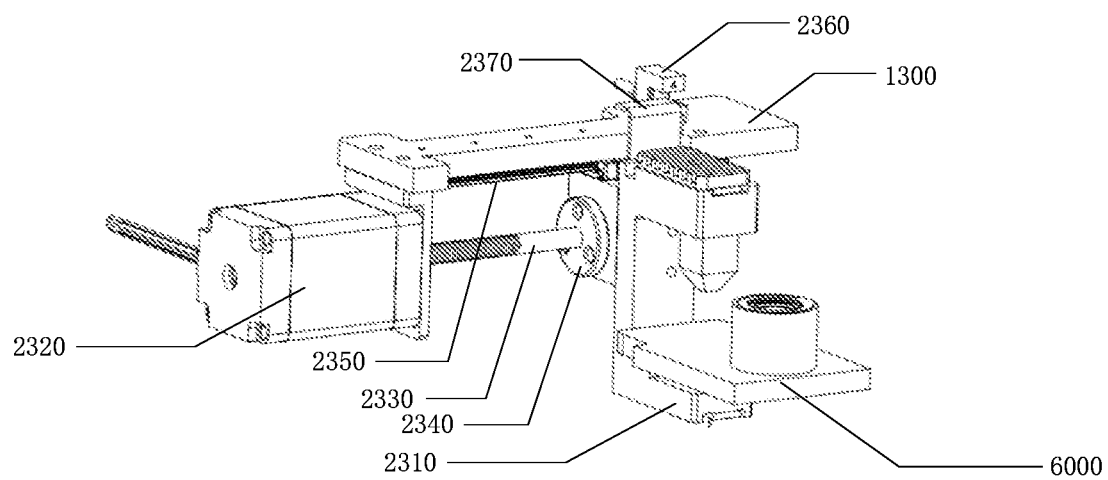
FIG. 10 is a schematic diagram of a movable detection component in a third position according to at least one embodiment of the present disclosure.

In the embodiments of the present disclosure, the movable detection component 2310 is driven by the third motor 2320 to move along the third guide rail 2350. A length of a moving stroke of the movable detection component 2310 can be determined according to actual requirements, for example, according to the width of the area to be detected of the specific microfluidic chip 6000 in a moving direction of the movable detection component 2310. In FIG. 9, the movable detection component 2310 is at one end of the moving stroke close to the third motor 2320. FIG. 10 is a schematic diagram of a movable detection component 2310 in a third position according to at least one embodiment of the present disclosure. The movable detection component 2310 can, for example, perform a fixed-point detection or a motion scanning detection such as an uninterrupted scanning detection on the microfluidic chip 6000, which is not limited in the embodiments of the present disclosure.

Figure 11:
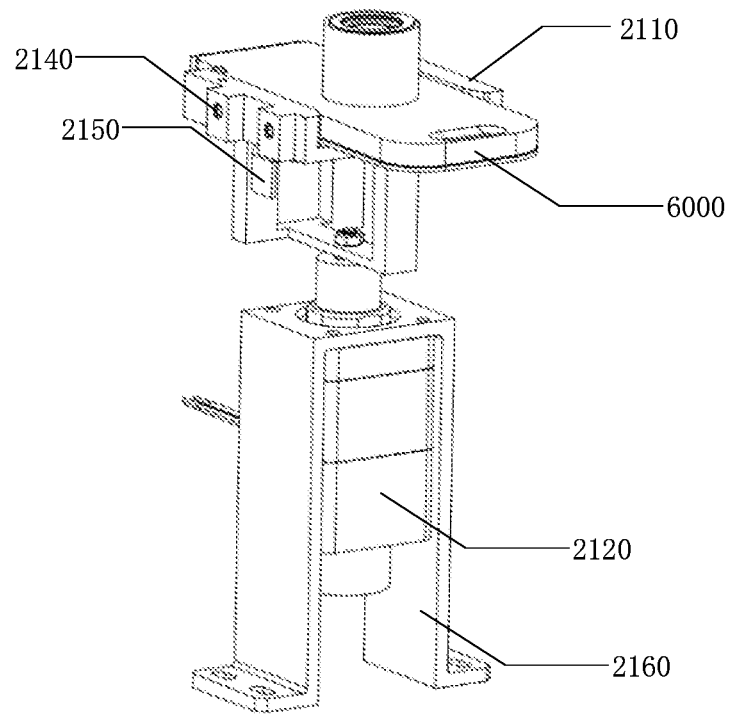
FIG. 11 is a structural schematic diagram of a position sub-module according to at least one embodiment of the present disclosure.

FIG. 11 is a structural schematic diagram of a positioning sub-module according to at least one embodiment of the present disclosure. The positioning sub-module of at least one embodiment of the present disclosure may include a accommodating structure, and the accommodating structure is configured to accommodate the microfluidic chip and can be driven to position the microfluidic chip. As illustrated in FIG. 11, the accommodating structure of the positioning sub-module 2100 may include a accommodating seat 2110, and the accommodating seat 2110 is configured to accommodate the microfluidic chip 6000. For example, the accommodating seat 2110 may fixedly mounted on the microfluidic chip in a proper way such as clamping, and the accommodating seat 2110 may be in an appropriate shape according to the shape of the microfluidic chip to be mounted. For example, the accommodating seat 2110 may be at least partially made of materials such as plastic, metal, etc. In some embodiments, the accommodating structure further includes a positioning element 2140. The positioning element 2140 is connected with the accommodating seat 2110 and is configured, in the case where the microfluidic chip 6000 is located on the accommodating seat 2110, to position the microfluidic chip 6000 in a releasable way. As illustrated in FIG. 11, the positioning element 2140 may include a ball plunger, and the ball plunger may be of conventional design, and is not described in detail in the present disclosure. In some other embodiments, the positioning element 2140 can also adopt other suitable structures, such as fastening screws, spring plates, etc., which are not limited in the embodiments of the present disclosure.

In some embodiments, the positioning sub-module 2100 further includes a fourth motor 2120 which is configured to drive the accommodating seat 2110 to move. In some embodiments, the fourth motor 2120 may be a linear motor, and the accommodating seat 2110 may be directly connected with the fourth motor 2120 without providing a transmission unit therebetween. However, the embodiments of the present disclosure are not limited thereto. In some other embodiments, the positioning sub-module 2100 may also adopt a combination of a rotating motor and a lead screw to drive the accommodating seat 2110 to move. In this case, the positioning sub-module 2100 may include a lead screw, a nut, a guide rail, etc. The specific structure of the positioning sub-module may be referred to the above-description of the first transmission unit, the second transmission unit, and the third transmission unit, and is not described in detail again.

In some embodiments, the positioning sub-module 2100 further includes a fourth position sensor 2130. The fourth position sensor 2130 is arranged on a moving path of the accommodating seat 2110 driven by the fourth motor 2120, and is configured, in the case where the accommodating seat 2110 is in a fourth position, to generate a fourth position signal for the fourth motor 2120. For example, the fourth position corresponds to an origin position of the fourth motor 2120, the fourth position signal is used to reset the fourth motor 2120, and the fourth position sensor 2130 can send the fourth position signal generated in the case where the accommodating seat 2110 is in the fourth position to the control module that controls the fourth motor 2120, so that the fourth motor 2120 is reset under the control of the control module. By arrangement of the fourth position sensor 2130, the origin position of the fourth motor 2120 can be reset, so that the accommodating seat 2110 can be accurately positioned.

In some embodiments, the first operation part 2210 and the second operation part 2220 may be arranged at opposite sides of the positioning sub-module 2100, the first fixing plate 1100 of the first operation part 2210 and the second fixing plate 1200 of the second operation part 2220 may face each other, and the fourth position sensor 2130 of the positioning sub-module 2100 may be arranged on a side surface of the second fixing plate 1200 of the second operation part 2220 facing the first fixing plate 1100 of the first operation part 2210, as illustrated in FIG. 6 to FIG. 8. However, it should be understood that the embodiments of the present disclosure are not limited thereto.

In some embodiments, the fourth position sensor 2130 may include a signal emitting part for emitting a detection signal and a signal receiving part for receiving the detection signal emitted by the signal emitting part, and the fourth position sensor 2130 may generate an indication signal in the case where the signal receiving part does not receive the detection signal emitted by the signal emitting part. In this case, the positioning sub-module 2100 may further include a fourth stopper piece 2150, and the fourth stopper piece 2150 can be fixedly connected with the accommodating seat 2110 so as to move synchronously with the accommodating seat 2110, and the fourth stopper piece 2150 is arranged between the signal emitting part and the signal receiving part of the fourth position sensor 2130 in the case where the accommodating seat 2110 is in the fourth position, so that the signal receiving part cannot receive the detection signal emitted by the signal emitting part, and thus the fourth position sensor 2130 generates the fourth position signal.

For example, the fourth position sensor 2130 may include a groove-type photoelectric switch, and the fourth stopper piece 2150 may be configured to be accommodated in the groove of the groove-type photoelectric switch and to prevent the signal emitted by a signal emitting end of the groove-type photoelectric switch from reaching a signal receiving end of the groove-type photoelectric switch. The fourth stopper piece 2150 can be manufactured by any suitable materials such as metal, wood, plastic, etc., as long as the fourth stopper piece 2150 can prevent the signal emitted by the signal emitting end of the groove-type photoelectric switch from reaching the signal receiving end of the groove-type photoelectric switch. However, it should be understood that the embodiments of the present disclosure are not limited thereto. For example, in some other embodiments, the fourth position sensor 2130 may also be a proximity sensor arranged at the fourth position, and in the case where the fourth position sensor 2130 detects that a distance between the fourth position sensor 2130 and the accommodating seat 2110 is less than a preset value, it is determined that the accommodating seat 2110 is at the fourth position.

Figure 12:
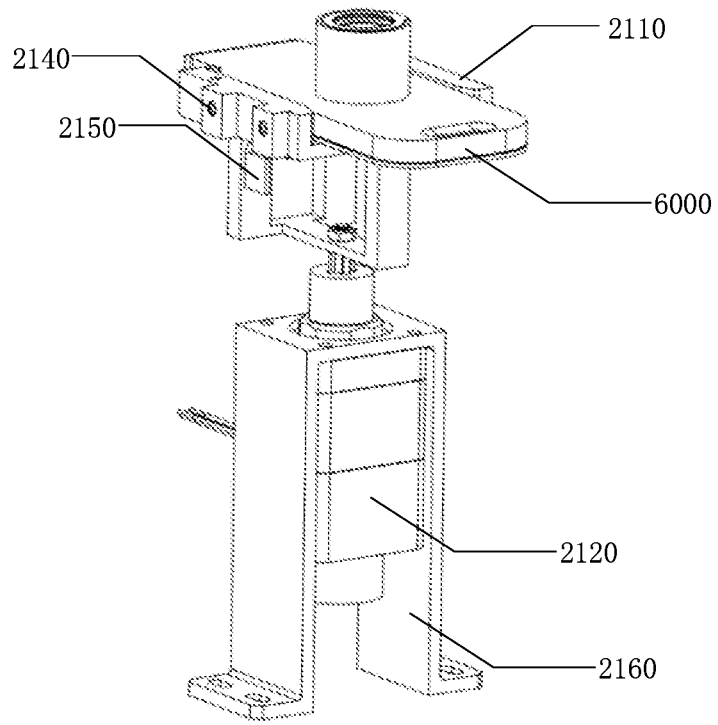
FIG. 12 is a schematic diagram of a accommodating seat in a fifth position according to at least one embodiment of the present disclosure.

In some embodiments, the accommodating seat 2110 can move between the fourth position and a fifth position under the drive of the fourth motor 2120. The accommodating seat 2110 is in the fourth position in FIG. 11, and FIG. 12 is a schematic diagram of the accommodating seat 2110 in the fifth position according to at least one embodiment of the present disclosure. In the case where the accommodating seat 2110 is in the fourth position, the accommodating seat 2110 is spaced apart from the fourth fixing plate 1400 which is matched (referring to FIG. 2) so as to accommodate the microfluidic chip. In the case where the accommodating seat 2110 is in the fifth position, the microfluidic chip on the accommodating seat 2110 can abut against the fourth fixing plate 1400. For example, in some embodiments, in the case where the accommodating seat 2110 is in the fifth position, the accommodating seat 2110 may be located at the farthest end of a moving stroke of the fourth motor 2120. It should be understood that the distance between the fourth position and the fifth position and the distance between the fifth position and the fourth fixing plate 1400 can be set according to actual requirements. The fourth fixing plate 1400 can be fixedly connected with the base 1000 so as to fix the microfluidic chip. In addition, the fourth fixing plate 1400 and the first movable rod 2211 are arranged at opposite sides of the microfluidic chip, thereby preventing the first movable rod 2211 from applying a force to the microfluidic chip in an opposite direction relative to the force applied to the microfluidic chip by the fourth fixing plate 1400.

In some embodiments, the positioning sub-module 2100 further includes a motor bracket 2160 fixed on the base 1000, and the fourth motor 2120 is fixed on the motor bracket 2160. However, it should be understood that the embodiments of the present disclosure are not limited to this, and in some other embodiments, for example, the fourth motor 2120 may also be directly fixed on the base 1000.

In some embodiments, as illustrated in FIG. 2, the first fixing plate 1100, the second fixing plate 1200, the third fixing plate 1300, and the fourth fixing plate 1400 may be fixed together or integrally formed. That is, the first fixing plate 1100, the second fixing plate 1200, the third fixing plate 1300, and the fourth fixing plate 1400 form the same fixing frame, and the fixing frame is fixed on the base 1000, so that the positioning sub-module 2100, the operation sub-module 2200, and the detection sub-module 2300 are fixed on the same fixing frame on the base 1000. In this way, the vibration of the analysis device can be reduced and the volume of the analysis device can be reduced. For another example, as illustrated in FIG. 2, the positioning sub-module 2100 and a plurality of operation parts (for example, the first operation part 2210 and the second operation part 2220) of the operation sub-module 2200 can be arranged side by side on the base 1000, for example, the positioning sub-module 2100 and the plurality of operation parts are basically arranged on the same line. As illustrated in FIG. 2, the positioning sub-module 2100 is sandwiched between the first operation part 2210 and the second operation part 2220, which is more conducive to the arrangement of the positioning sub-module 2100 and the operation sub-module 2200, thereby allowing the internal structure of the analysis device to be more compact, and being conducive to the miniaturization of the analysis device.

Referring to FIG. 1, the analysis device for the microfluidic chip according to at least one embodiment of the present disclosure further includes a processing module 3000, a power supply module 4000, and an interface module 5000, and the processing module 3000, the power supply module 4000, and the interface module 5000 are all arranged on the base 1000. In some embodiments, the processing module 3000 and the interface module 5000 may be arranged adjacent to each other, the control module 2000 may be arranged adjacent to the processing module 3000, and/or the power supply module 4000 may be arranged adjacent to the processing module 3000, so that the length of an internal wiring of the analysis device is reduced. In addition, in some embodiments, in the direction perpendicular to a surface of the base 1000 carrying these modules, the power supply module 4000 may partially overlap with at least one selected from the group consisting of the control module 2000 and the processing module 3000, so that the internal structure of the analysis device is more compact, thereby being conducive to the miniaturization of the analysis device. Similarly, in some embodiments, in the direction perpendicular to the surface of the base 1000 carrying these modules, the control module 2000 may partially overlap with the processing module 3000, so that the internal structure of the analysis device is more compact, thereby being conducive to the miniaturization of the analysis device.

The processing module 3000 is in signal connection with the control module 2000, and is configured to provide a control instruction to the control module 2000 so as to control the operation of the control module 2000. For example, the processing module 3000 can receive and process at least one selected from the group consisting of the first position signal, the second position signal, the third position signal, and the fourth position signal, and can provide a control instruction to at least one selected from the group consisting of the first motor 2212, the second motor 2222, the third motor 2320, and the fourth motor 2120, so that at least one selected from the group consisting of the first motor 2212, the second motor 2222, the third motor 2320, and the fourth motor 2120 starts or stops operation. In addition, in some embodiments, the processing module 3000 may include a processor and a control circuit board. The processor is configured to generate instructions and to provide the instructions to the control circuit board, and the control circuit board is configured to receive the instructions from the processor and to send execution instructions to an execution module (such as the control module 2000) so as to control the movement of the motor, collect and process of signals, and provide processed signals to the processor. For example, the processor may include, but is not limited to, a central processing unit (CPU), a digital signal processor (DSP), a field programmable gate array (FPGA), a program specific integrated circuit (ASIC), a program specific standard product (ASSP), a system on a chip (SOC), a complex programmable logic device (CPLD), or a combination thereof. The control circuit may include, but is not limited to, a motor drive board, a signal acquisition board, etc.

The power supply module 4000 is configured to provide electric power for the control module 2000 and the processing module 3000. The power supply module 4000 may have the function of a transformer, for example, to convert alternating current of 220V or 110V into direct current of 12V or 24V, and provide the direct current to the control module 2000 and the processing module 3000. The power supply module 4000 may also be a power generation device, a storage battery, a photovoltaic cell, a rechargeable battery or any other device capable of providing electrical energy, which is not limited in the embodiments of the present disclosure. Furthermore, in some embodiments, the power supply module 4000 can be detachably attached relative to the analysis device.

The interface module 5000 is in signal connection with the processing module 3000, and the processing module 3000 communicates with an external equipment through the interface module 5000. For example, the interface module may include, but is not limited to, a power supply interface, a data interface, etc. The power supply interface may be configured for electric power, and the data interface is configure to realize communication between the analysis device and the external equipment. The external equipment may be, for example, a laboratory information system or a hospital information system.

The analysis device for the microfluidic chip provided by the embodiments of the present disclosure can reduce the occupied space, realize the portability of instruments, and improve the simplicity of detection.

Figure 13:
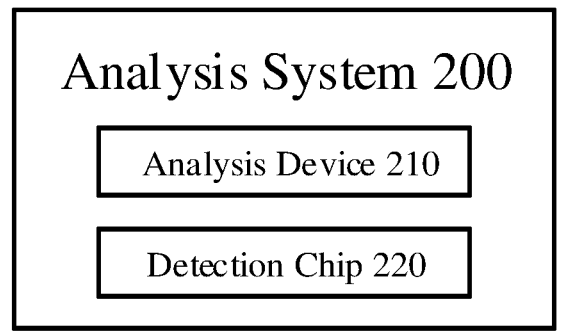
FIG. 13 is a schematic block diagram of an analysis system according to at least one embodiment of the present disclosure.

FIG. 13 is a schematic block diagram of an analysis system according to at least one embodiment of the present disclosure. As illustrated in FIG. 13, an analysis system 200 includes an analysis device 210 and a detection chip 220. For example, the analysis device 210 and the unused detection chip 220 can be combined and provided to a user for usage. The analysis device 210 may be any one of the analysis devices described above. The detection chip 220 may be any one of the detection chips described above.

It should be understood that in some embodiments of the present disclosure, the analysis system 200 may further include more components or parts, and the embodiments of the present disclosure are not limited to this. For the detailed description and technical effects of the analysis device 210 and the detection chip 220, reference can be made to the description of the analysis device in any one of the above embodiments, which are not repeated here.

At least one embodiment of the present disclosure also provides a method for operating an analysis device. The method is applicable to the analysis device according to any embodiment of the present disclosure.

Figure 14:
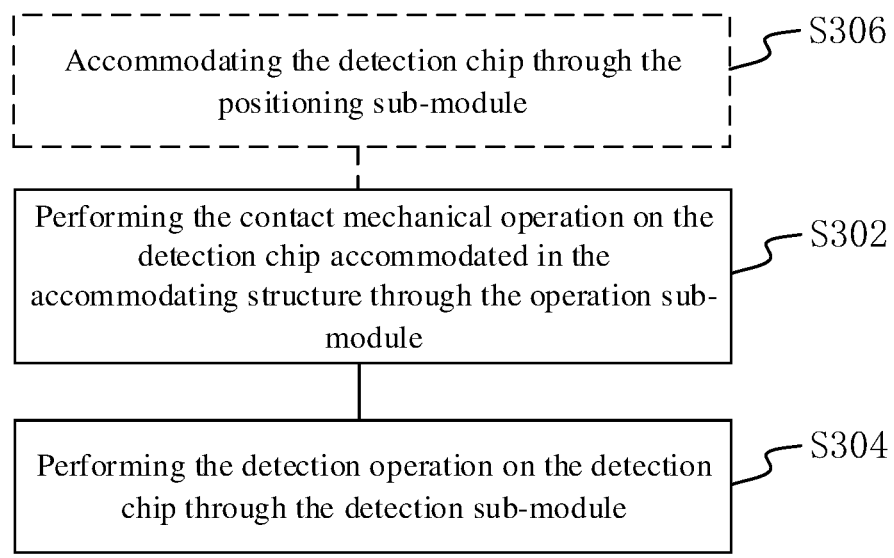
FIG. 14 is a schematic flowchart of a method for operating an analysis device according to at least one embodiment of the present disclosure.

FIG. 14 is a schematic flowchart of a method for operating an analysis device according to at least one embodiment of the present disclosure. As illustrated in FIG. 14, the method for operating the analysis device according to at least one embodiment of the present disclosure may include following steps.

S302: performing the contact mechanical operation on the detection chip accommodated in the accommodating structure through the operation sub-module.

S304: performing the detection operation on the detection chip through the detection sub-module.

For example, in at least one embodiment, at least one operation part of the operation sub-module of the analysis device includes a first operation part, and the first operation part includes a first movable rod. In the case where the first movable rod includes a first operation end portion, step S302 may further include: driving the first operation end portion to a release operation position, so that the first operation end portion performs a release operation on the detection chip.

For the specific implementation and technical effects of the first operation part, the first movable rod, and the first operation end portion, reference can be made to the specific implementation and technical effects of the first operation part 2210, the first movable rod 2211, and the first operation end portion 2211' in the above embodiments, which are not described in detail in the embodiments of the present disclosure.

For example, in at least one embodiment, in the case where the first operation part further includes a first motor and a first transmission unit, above-mentioned driving the first operation end portion to the release operation position so that the first operation end portion performs the release operation on the detection chip may include: transmitting the motion provided by the first motor to the first movable rod through a first transmission unit so as to drive the first movable rod.

For the specific implementation and technical effects of the first motor and the first transmission unit, reference can be made to the specific implementation and technical effects of the first motor 2212 and the first transmission unit in the above embodiments, which are not described in detail in the embodiments of the present disclosure.

For example, in at least one embodiment, in the case where at least one operation part of the operation sub-module of the analysis device includes a second operation part, the second operation part includes a second movable rod, and the second movable rod includes a second operation end portion, step S302 may further include: driving the second operation part to a pressing operation position so as to perform a pressing operation on the detection chip through the second operation end portion.

For the specific implementation and technical effects of the second operation part, the second movable rod, and the second operation end portion, reference can be made to the specific implementation and technical effects of the second operation part 2220, the second movable rod 2221, and the second operation end portion 2221' mentioned above, which are not described in detail in the embodiments of the present disclosure.

For example, in at least one embodiment, in the case where the second operation part further includes a second motor and a second transmission unit, the above-mentioned driving the second operation part to the pressing operation position so as to perform a pressing operation on the detection chip through the second operation end portion may include: transmitting the motion provided by the second motor to the second movable rod through the second transmission unit so as to drive the second movable rod.

For the specific implementation and technical effects of the second motor and the second transmission unit, reference can be made to the specific implementation and technical effects of the second motor 2222 and the second transmission unit in the above embodiments, which are not described in detail in the embodiments of the present disclosure.

For example, in at least one embodiment, in the case where the detection sub-module includes a movable detection component, the above-described step S304 may include: driving the movable detection component to move relative to the detection chip and performing the detection operation through the movable detection component.

For the specific implementation and technical effects of the movable detection component, reference can be made to the specific implementation and technical effects of the movable detection component 2310 in the above embodiments, which are not described in detail in the embodiments of the present disclosure.

For example, in at least one embodiment, in the case where the detection sub-module further includes a third motor and a third transmission unit, the above-described driving the movable detection component to move relative to the detection chip and performing the detection operation through the movable detection component may include: transmitting the motion provided by the third motor to the movable detection component through the third transmission unit so as to drive the movable detection component.

For the specific implementation and technical effects of the third motor and the third transmission unit, reference can be made to the specific implementation and technical effects of the third motor 2320 and the third transmission unit in the above embodiments, which are not described in detail in the embodiments of the present disclosure.

For example, the method for operating the analysis device according to at least one embodiment of the present disclosure may further include following steps.

S306: accommodating the detection chip through the positioning sub-module.

Step S306 may be performed before step S302.

The method for operating the analysis device according to at least one embodiment of the present disclosure can achieve technical effects similar to those of the analysis devices provided in the above embodiments, which are not described in detail in the embodiments of the present disclosure.

What have been described above are only specific implementations of the present disclosure, the protection scope of the present disclosure is not limited thereto, and the protection scope of the present disclosure should be based on the protection scope of the claims.

What is claimed is:

1. An analysis device for a detection chip, comprising:
   a base; and
   a control module, provided on the base and comprising:
      a positioning sub-module, wherein the positioning sub-module comprises an accommodating structure, and the accommodating structure is configured to accommodate the detection chip;
      an operation sub-module, wherein the operation sub-module comprises at least one operation part, and the at least one operation part is configured to be driven to perform a contact mechanical operation on the detection chip; and
      a detection sub-module, configured to perform a detection operation on a sample in the detection chip,
   wherein the at least one operation part of the operation sub-module comprises a first operation part and a second operation part,
   the first operation part comprises a first movable rod, and the first movable rod comprises a first operation end portion and is configured to be driven to a release operation position, so that the first operation end portion performs a release operation on the detection chip,
   the second operation part comprises a second movable rod, and the second movable rod comprises a second operation end portion and is configured to be driven to a pressing operation position so as to perform a press operation on the detection chip through the second operation end portion,
   the first operation part and the second operation part are located on two opposite sides of the accommodating structure of the positioning sub-module, and a direction in which the first movable rod moves toward the detection chip is opposite to a direction in which the second movable rod moves toward the detection chip.

2. The analysis device according to claim 1, wherein the first operation part further comprises:
   a first motor; and
   a first transmission unit, connected with the first motor and the first movable rod and configured to transmit a motion provided by the first motor to the first movable rod so as to drive the first movable rod.

3. The analysis device according to claim 2, wherein the first transmission unit comprises:
   a first lead screw, connected with the first motor and configured to rotate under drive of the first motor;
   a first lead screw supporting seat, wherein the first lead screw is connected between the first lead screw supporting seat and the first motor;
   a first nut, threadedly engaged with the first lead screw and fixedly connected with the first movable rod, wherein the first nut is configured, in a case where the first lead screw rotates, to move on the first lead screw; and
   a first guide rail, wherein the first movable rod is capable of moving along the first guide rail.

4. The analysis device according to claim 2,
   wherein the first operation part further comprises a first position sensor, and
   the first position sensor is configured, in a case where the first movable rode is in a first position, to generate a first position signal for the first motor.

5. The analysis device according to claim 1, wherein the second operation part further comprises:
   a second motor, configured to drive the second movable rod to move back and forth; and
   a second transmission unit, connected with the second motor and the second movable rod and configured to transmit a motion provided by the second motor to the second movable rod so as to drive the second movable rod.

6. The analysis device according to claim 5, wherein the second transmission unit comprises:
   a second lead screw, connected with the second motor and configured to rotate under drive of the second motor;
   a second lead screw supporting seat, wherein the second lead screw is connected between the second lead screw supporting seat and the second motor;
   a second nut, threadedly engaged with the second lead screw and fixedly connected with the second movable rod, wherein the second nut is configured, in a case where the second lead screw rotates, to move on the second lead screw; and
   a second guide rail, wherein the second movable rod is capable of moving along the second guide rail.

7. The analysis device according to claim 5,
   wherein the second operation part further comprises a second position sensor, and
   the second position sensor is configured, in a case where the second movable rod is in a second position, to generate a second position signal for the second motor.

8. The analysis device according to claim 1,
   wherein the detection sub-module comprises a movable detection component, and
   the movable detection component is provided with a U-shaped structure, and is configured to accommodate the detection chip in an opening of the U-shaped structure, move relative to the detection chip, and perform the detection operation.

9. The analysis device according to claim 8, wherein the detection sub-module further comprises:
- a third motor, configured to drive the movable detection component to move; and
- a third transmission unit, connected with the third motor and the movable detection component and configured to transmit a motion provided by the third motor to the movable detection component so as to drive the movable detection component.

10. The analysis device according to claim 9, wherein the third transmission unit comprises:
- a third lead screw, connected with the third motor and configured to rotate under drive of the third motor;
- a third nut, threadedly engaged with the third lead screw and fixedly connected with the movable detection component, wherein the third nut is configured, in a case where the third lead screw rotates, to move on the third lead screw; and
- a third guide rail, wherein the movable detection component is capable of moving along the third guide rail.

11. The analysis device according to claim 9,
wherein the detection sub-module further comprises a third position sensor, and
the third position sensor is configured, in a case where the movable detection component is in a third position, to generate a third position signal for the third motor.

12. The analysis device according to claim 1,
wherein the accommodating structure comprises an accommodating seat, and
the positioning sub-module further comprises:
- a fourth motor, configured to drive the accommodating seat to move; and
- a fourth position sensor, provided at a moving path of the accommodating seat driven by the fourth motor and configured, in a case where the accommodating seat is in a fourth position, to generate a fourth position signal for the fourth motor.

13. The analysis device according to claim 12,
wherein the accommodating seat is configured to move between the fourth position and a fifth position under drive of the fourth motor;
at the fourth position, the accommodating seat is spaced apart from a fixing plate that is matched with the accommodating seat so as to accommodate the detection chip; and
at the fifth position, the detection chip is capable of abutting against the fixing plate.

14. The analysis device according to claim 12,
wherein the accommodating structure further comprises a positioning element, and
the positioning element is connected with the accommodating seat and is configured, in a case where the detection chip is on the accommodating seat, to position the detection chip in a releasable way.

15. The analysis device according to claim 14, wherein the positioning element comprises a ball plunger.

16. The analysis device according to claim 1, wherein the positioning sub-module, the operation sub-module, and the detection sub-module are fixed on a same fixing frame on the base.

17. An analysis system, comprising:
- a detection chip; and
- the analysis device according to claim 1.

18. A method for operating the analysis device according to claim 1, comprising:
- performing the contact mechanical operation on the detection chip accommodated in the accommodating structure through the operation sub-module; and
- performing the detection operation on the detection chip through the detection sub-module.

* * * * *